US010576349B2

(12) United States Patent
Edralin et al.

(10) Patent No.: US 10,576,349 B2
(45) Date of Patent: Mar. 3, 2020

(54) SYSTEM AND METHODS OF OBJECTIVELY EVALUATING FOOTBALL PLAYER TACKLING PERFORMANCE

(71) Applicant: Rugby Nation, LLC, Seattle, WA (US)

(72) Inventors: Justin Kealii Edralin, Seattle, WA (US); Adam Michael Kopp, Camano Island, WA (US); Rex Delre Norris, Jr., Covington, WA (US)

(73) Assignee: Rugby Nation, LLC, Seattle, WA (US)

( * ) Notice: Subject to any disclaimer, the term of this patent is extended or adjusted under 35 U.S.C. 154(b) by 0 days.

(21) Appl. No.: 15/897,067

(22) Filed: Feb. 14, 2018

(65) Prior Publication Data
US 2018/0304139 A1    Oct. 25, 2018

Related U.S. Application Data

(60) Provisional application No. 62/459,548, filed on Feb. 15, 2017.

(51) Int. Cl.
| A63B 69/34 | (2006.01) |
| G06T 7/292 | (2017.01) |
| G06K 9/00 | (2006.01) |
| A61B 5/11 | (2006.01) |

(52) U.S. Cl.
CPC ........ A63B 69/345 (2013.01); G06K 9/00342 (2013.01); G06T 7/292 (2017.01); *A61B 5/1122* (2013.01); *A61B 5/1128* (2013.01); *A61B 2503/10* (2013.01); *A63B 2220/806* (2013.01); *A63B 2243/007* (2013.01); *G06T 2207/30221* (2013.01)

(58) Field of Classification Search
CPC ............ A63B 69/345; A63B 2243/007; A63B 2220/806; G06T 7/292; G06T 2207/30221
See application file for complete search history.

(56) References Cited

U.S. PATENT DOCUMENTS

| 2,943,141 | A | * | 6/1960 | Knight | ............... | A63B 71/0605 |
| | | | | | | 348/157 |
| 6,710,713 | B1 | * | 3/2004 | Russo | ................ | A63B 24/0021 |
| | | | | | | 340/573.1 |
| 2011/0013087 | A1 | * | 1/2011 | House | ................ | A63B 24/0021 |
| | | | | | | 348/564 |
| 2011/0294101 | A1 | * | 12/2011 | DeStefano | ........... | A63B 69/004 |
| | | | | | | 434/251 |

* cited by examiner

*Primary Examiner* — Eugene L Kim
*Assistant Examiner* — Jeffrey S Vanderveen
(74) *Attorney, Agent, or Firm* — Perkins Coie LLP (57) ABSTRACT

A system is provided for evaluating football player tackling performance of learned skills in a competitive in-game setting. The system includes reviewing video footage of football games, and analyzing each tackle opportunity with clear objectives for the player with the tackling opportunity to satisfy to achieve a successful result. The system also includes a visual tool that provides clear context for analysis of each tackle opportunity. Methods of evaluation are also provided.

11 Claims, 12 Drawing Sheets

Figure 1 – The tackle circle.

Figure 2 – A competent angle tackle.

Figure 3 – A competent chase tackle.

Figure 4 – An example of a cut tackle.

Figure 5 – An example of a profile tackle.

Red arrows show direction to tackling player's end zone

Figure 6 – An example of a heel tackle.

701

702

703

704

705

Figure 7 – Using still images from post-game video, applying the tackle wheel (703) to determine a negative situation, a roll tackle type, and that the play resulted in the ball carrier gained one yard after contact (-1 YAC) (705).

Figure 8 – A tackling player performing a drill exemplifying good tackle height, arm extension, and use of near shoulder.

Figure 9 – A tackling player with spine in line while initiating contact with ball carrier.

Figure 10 – Tackling player showing good hip extension through contact with ball carrier.

Figure 11 – Tackling player poorly executing wrap and squeeze.

Figure 12 – An example of a competently performed leg drive element of the tackle form score.

Figure 13 – Example of poor execution closing space and moving to avoid obstacles (the block).

Figure 14 – Another example of poor execution of the closing space element of tracking.

Figure 15 – Example of a poor choice of angle to gain leverage and close space on ball carrier.

1601          1602

Figure 16 – Poor execution of tracking the near hip of the ball carrier, resulting in over-pursuit and a missed tackle.

Figure 17 – Poor execution of maintaining effective footwork.

Grading the Track Performance: Track is to maximize contact with the ball carrier

| | 4 = Dominant Contact | 3 = Efficient Contact | 1 = Poor Contact | 0 = No Contact |
|---|---|---|---|---|
| Positive Situation | Maximized contact<br>Executing all track zones<br><br>Video Analysis<br>Look for:<br>Body / Shoulder contact / Power Step | Major Contact<br>Errors in Footwork and/or Leverage<br><br>Video Analysis<br>Look for:<br>Body / Shoulder contact | Limited Contact<br>Errors in Leverage and/or Closing<br><br>Video Analysis<br>Look for:<br>Arm and hand contact with ability to grab | Limited or No Contact<br>Error in Closing Space<br><br>Video Analysis<br>Look for:<br>Hand contact or no contact |
| | 3 = Efficient Contact | 2 = Cover Track | 1 = Recovery Track | 0 = No Contact |
| Negative Situation | Major Contact<br>Executing all three Zones despite the negative situation<br><br>Video Analysis<br>Look for:<br>Body / Shoulder contact | Limited Contact<br>Made contact with limited time & space, or beyond their responsibility<br><br>Video Analysis<br>Look for:<br>Arm and hand contact with ability to grab | Limited Contact<br>Tackler made play despite initial poor execution<br><br>Video Analysis<br>Look for:<br>Arm and hand contact with ability to grab | Limited or No Contact<br>Error in Closing Space<br><br>Video Analysis<br>Look for:<br>Hand contact or no contact |

Grading the Tackle Performance: Tackle is to maximize power and control over the ball carrier

| | 4 = Dominant Tackle | 3 = Efficient Tackle | 1 = Poor Tackle | 0 = Missed Tackle |
|---|---|---|---|---|
| Positive Situation | Maximized power and control<br>Dominated the contact point<br><br>Video Analysis<br>Look for:<br>Momentum of offensive went backwards / caused fumble | Maintain Power and Control<br>Limited yards after contact<br><br>Video Analysis<br>Look for:<br>Tackle made limiting YACs to 0 – 1 yard | Gave away Power and Control<br>Offense took advantage of contact point<br><br>Video Analysis<br>Look for:<br>Tackle made resulting in 2+ YACs | Lost Power and Control<br>Ball carrier dominated contact opportunity<br><br>Video Analysis<br>Look for:<br>Missed tackle with or without contact |
| | 3 = Efficient Tackle | 2 = Cover Tackle | 1 = Recovery Tackle | 0 = Missed Tackle |
| Negative Situation | Maintain Power and Control<br>Limited yards after contact<br><br>Video Analysis<br>Look for:<br>Tackle made limiting YACs to 0 – 1 yard | Gave away Power and Control<br>Offense took advantage of contact point<br><br>Video Analysis<br>Look for:<br>Tackle made resulting in 2+ YACs | Gave away Power and Control<br>Offense took advantage of contact point<br><br>Video Analysis<br>Look for:<br>Tackle made resulting in 2+ YACs | Lost Power and Control<br>Ball carrier dominated contact opportunity<br><br>Video Analysis<br>Look for:<br>Missed tackle with or without contact |

Figure 18 – Performance Score Table for positive/negative situation track and tackle results.

Our grading system generates a final 'Dominance grade' or ATAVUS Dominance Score. The score will be a combination of technique execution and performance.

$T_R$ = Track Form Score $T_A$ = Tackle Form Score $P$ = Performance Score $W$ = Weighted element (% weighting on part of overall score)

$$\text{Overall score} = T_R (W_{Tr}) + T_A (W_{Ta}) + P (W_P)$$

*Once each score is converted to a 100 point scale and the weight for each element has been applied, we add the three pieces together (scores 1, 2 and 3) to arrive at the Overall score*

Figure 19 – Generating the overall score using weighting factors and track form, tackle form, and performance scores.

Figure 20 – A team summary from one game.

Figure 21 – Example report from online portal where tackle efficiency analysis is delivered to coaches.

SYSTEM AND METHODS OF OBJECTIVELY EVALUATING FOOTBALL PLAYER TACKLING PERFORMANCE

CROSS REFERENCE TO RELATED APPLICATION

This application claims the benefit of the filing date of U.S. Provisional Patent Application Ser. No. 62/459,548 filed Feb. 15, 2017, which is hereby incorporated by reference in its entirety.

BACKGROUND

The game of American football (football) is played in different leagues across North America, and elsewhere in the world. While rules and other aspects of the game very from league to league, some of the fundamentals remain the same across the different leagues. For example, the field dimensions and position of the goalpost uprights are just two of the differing aspects between notable U.S. leagues—the NFL and NCAA—and Canadian football leagues. See rulebooks for NFL—http://operations.nfl.com/the-rules/2016-nfl-rulebook/, NCAA—http://www.ncaa.org/championships/playing-rules/football-rules-game, and the CFL—https://cfldb.ca/rulebook/. Similarities are abundant though, and one similarity is the occurrence of a defender or special team player performing the act of tackling the ball carrier on the opposing team. The act of tackling is defined in each set of the above rulebooks: NFL—Rule 3, Section 35; NCAA—Rule 2, Section 26; CFL—Statistical Scoring Rules, Section 18. Across these three leagues, which are used for example purposes and not intended to represent an exhaustive list of football league organizations, the act of tackling includes the ball carrier's movement on the field being stopped due to some level of contact by a player from the opposing team attempting a tackle.

BRIEF SUMMARY

System and methods of objectively evaluating a football player's performance of executing the act of tackling another player.

BRIEF DESCRIPTION OF THE SEVERAL VIEWS OF THE DRAWINGS

FIG. 18—Performance Score Table for positive/negative situation track and tackle results.

DETAILED DESCRIPTION

Though the act of tackling applies to many forms of football, players execute the act with varying levels of proficiency. Measuring this proficiency for individual players will provide information for individual player tackling efficiency. It may be important from a coaching, player management, and player perspective to have information about a player's tackling efficiency. If the act is broken down into component steps, and the player's performance objectively evaluated, a player or team's particular strengths and weaknesses can be identified, and mitigated or exploited. For example, a player who does not possess great speed in their movements, but rarely misses a tackle if he or she can get a hand on the ball carrier could benefit from positional adjustment or specific training that will be different from a player with similar tackling efficiency who possesses great speed, but misses tackles after making contact with the ball carrier. Furthermore, tackling efficiency also takes importance from a broader perspective. When a tackle is performed in accordance with training that minimizes the opportunity for significant impact to the tackling player's head or other body part, it can allow a player to participate in more plays, and make more tackles. Missing plays due to health or injury issues is not equated to missing a tackle on the field, but can be considered a missed opportunity for the affected player to make a tackle.

Objective evaluation of player performance regarding specific training can be achieved by establishing a framework for scoring player performance while minimizing the potential for subjectivity in the scoring. A framework should include elements of skills taught to perform in an efficient manner, and criteria used to evaluate those skills should be clear, demonstrable, and objective. The framework will not take into account any individual player's special talents or limitations. For example, a player who competes while dealing with injury in some way and performs poorly will not have a different scoring system applied to their performance.

In some embodiments, a player will be scored within the framework if the outcome of a play may be reliably observed on post-game video and results in the ball carrier being tackled by one or more players. Generally, a tackling player's scoring begins when that player is observed on post-game video to make an effort to engage the ball carrier, and either makes a tackle of the ball carrier, or through improved execution of track form and/or tackle form elements, would have tackled the ball carrier. A player will be determined to have made an effort to engage the ball carrier if the post-game video shows that player to have seen the ball carrier and moved on a track to engage the ball carrier, even if done poorly.

In some embodiments, situations may result in a player being scored, even though a tackle of the ball carrier is not completed. For example, player scoring will occur when: the potential tackler has an opportunity to tackle the quarterback prior to the quarterback completing a pass, with negative implications regarding the statistics of the completed pass counting against the tackler who missed; the ball carrier is forced out of bounds, which results in a track form score, but no tackle form score; a tackle is made on a play resulting in a penalty call on either team; the potential tackler contacts the ball carrier by manipulating another offensive player into the ball carrier.

In some embodiments, the outcome of a play may in some cases result in no scoring since the performance of any player cannot be reliably graded. For example, no player scoring occurs when: the result of the play cannot be observed (the result of a short yardage run where the tackling player and ball carrier were obstructed in the post-game video and the aftermath is a heap of players); the ball carrier either slides or falls and is ruled down without having been influenced by a tackler; the ball carrier runs out of bounds without influence by a tackler.

Figure 1:
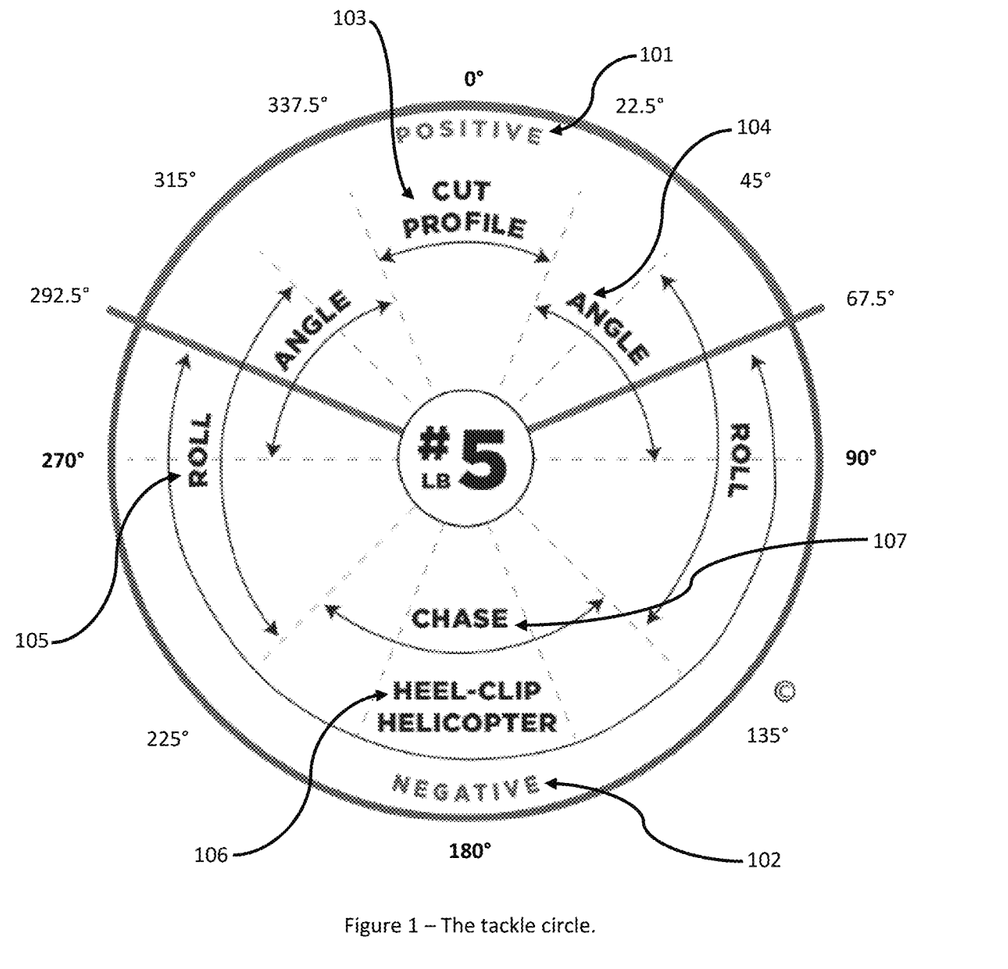
FIG. 1—The tackle circle.
Figure 7:
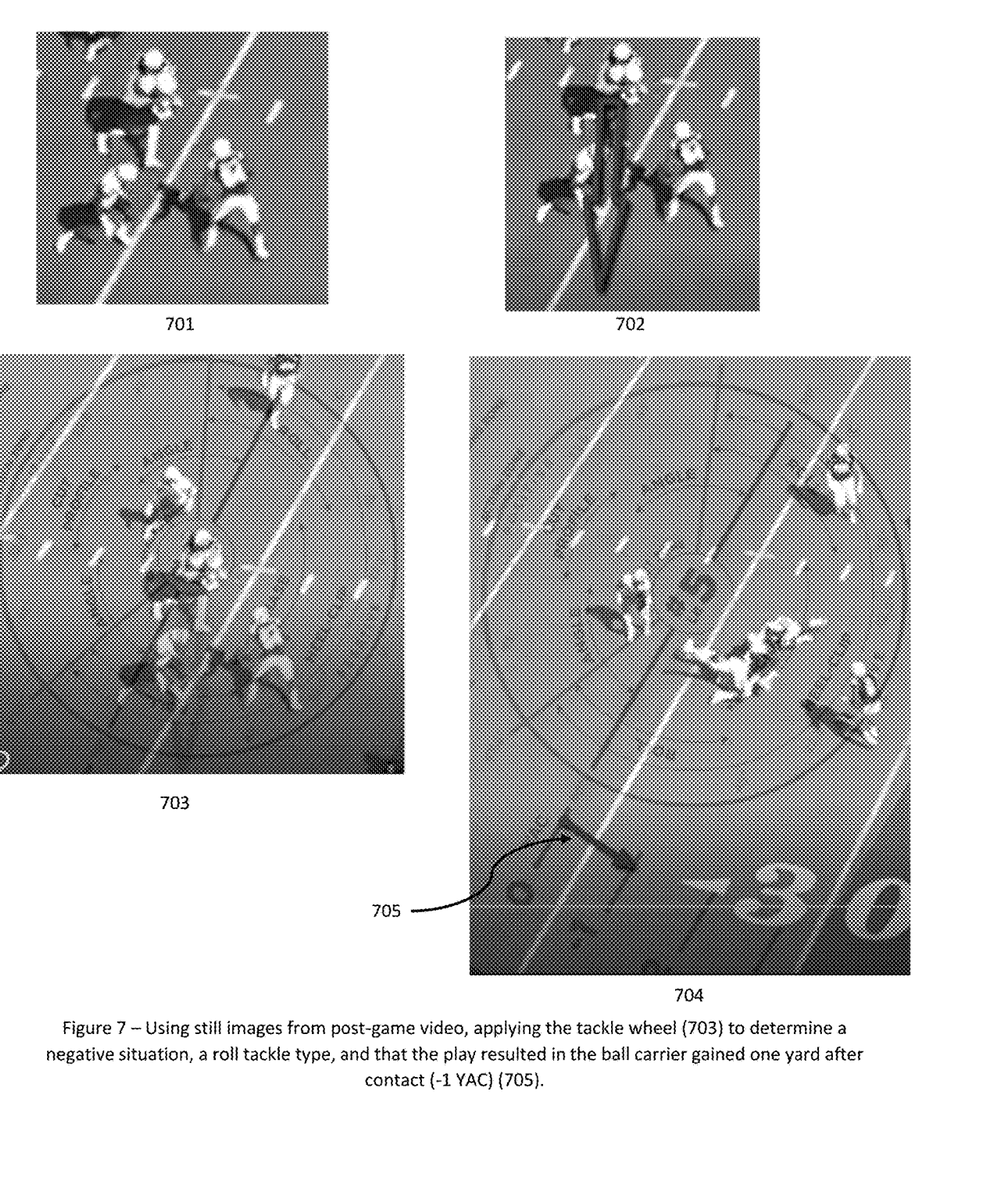
FIG. 7—Using still images from post-game video, applying the tackle wheel (703) to determine a negative situation, a roll tackle type, and that the play resulted in the ball carrier gained one yard after contact (−1 YAC) (705).
Figure 8:
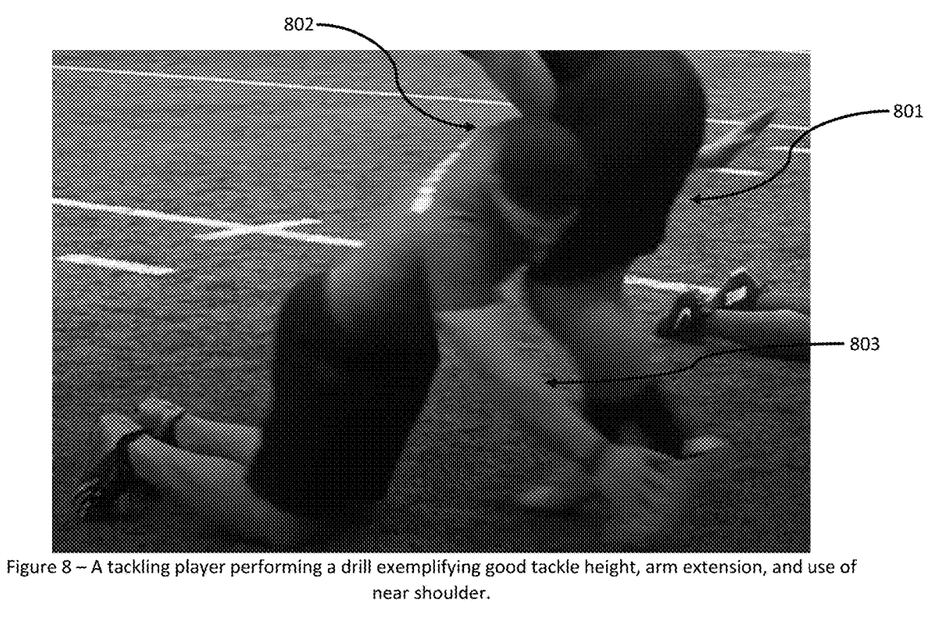
FIG. 8—A tackling player performing a drill exemplifying good tackle height, arm extension, and use of near shoulder.
Figure 9:
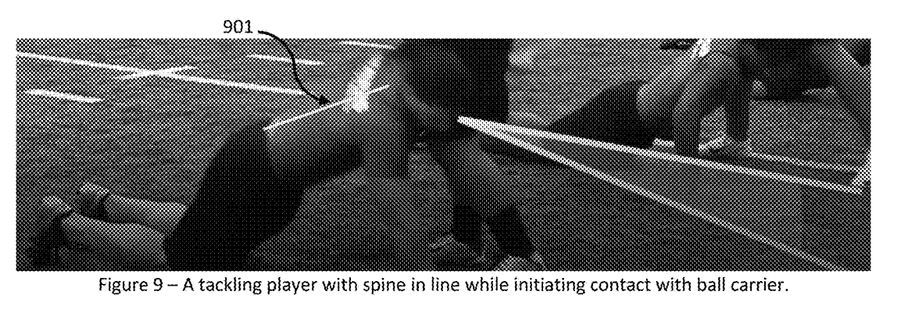
FIG. 9—A tackling player with spine in line while initiating contact with ball carrier.

In some embodiments, whether a positive or negative outcome situation is being evaluated can be determined by using a tackle circle. One example of a tackle circle is given in FIG. 1. A tackle circle has markings that help the scorer determine whether the tackling player was making tackle from a position in front, to the side, or behind the ball carrier. A scorer may use the tackle circle by: observing on post-game video where initial contact between the tackling player and the ball carrier is made 701, pausing playback of the post-game video, placing the center of the tackle circle on the tackling player when the tackling player makes initial contact with the ball carrier, centering the inner circle on the tackling player and having the ball carrier located near the edge of the circle, with the tackle circle oriented such that: it is co-planar with the surface of the playing field, a line running through the center of the circle, the 900 and 270° line of the circle, runs perpendicular to the sidelines and parallel to the on-field yard lines, and the 180° point of the circle is located closer to the end zone being defended by the tackling player than any other point on the circle 703. The position of the ball carrier is then located within the tackle circle, and specifically, whether the ball carrier is within the zone of positive outcomes 101, or the zone of negative outcomes 102. Furthermore, in the area between the 67.5° and 90° lines of the circle and the 270° and 292.5° lines of the circle, where three different tackle types may commonly occur, the determination of scoring the player either in a positive outcome or a negative outcome situation depends on the type of tackle the play results in. For example, after orienting the tackle circle, an angle tackle made on a ball carrier situated at an 80° from the tackling player at the point of initial contact may be scored as a positive outcome situation. Conversely, if the tackling player and the ball carrier were in the same positions and the play resulted in a roll or heel tackle, the play may be scored as a negative outcome situation. Placing the tackle circle at the point where initial contact is made also helps the scorer measure yards gained or lost by the ball carrier after initial contact 705.

Figure 2:
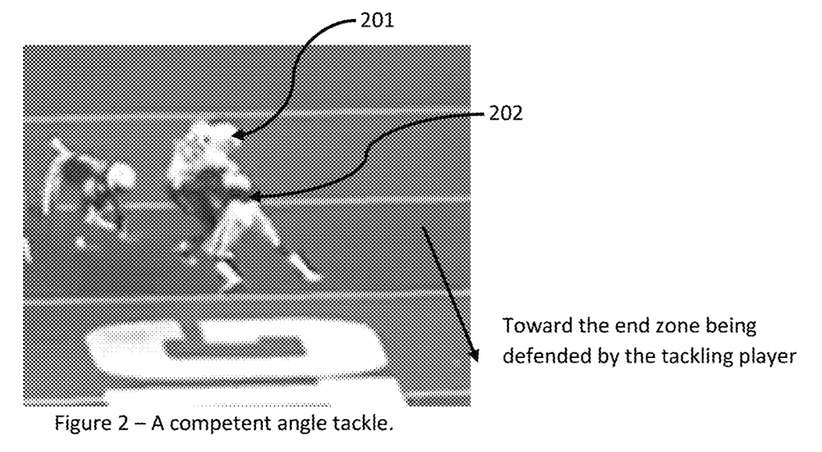
FIG. 2—A competent angle tackle.
Figure 4:
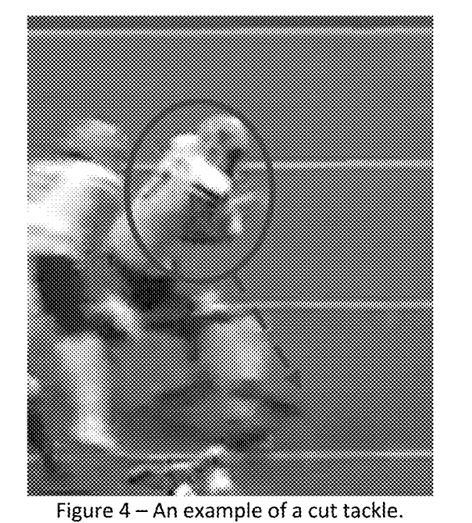
FIG. 4—An example of a cut tackle.
Figure 5:
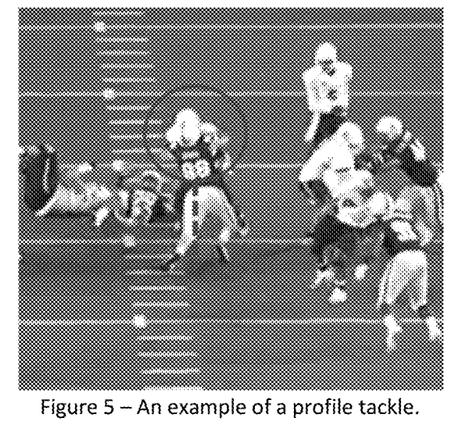
FIG. 5—An example of a profile tackle.

In some embodiments, a situational adjustment to the scoring may be made depending on the tackle type made. Certain tackle types are made with the ball carrier positioned upfield from the tackling player, meaning that the ball carrier would be in front of the tackling player with the ball carrier facing the end zone being defended by the tackling player, while the ball carrier is closer to the end zone being defended by the ball carrier's team than the tackling player is, and the tackling player facing the end zone being defended by the ball carrier's team while being closer to the end zone the tackling player is defending than the ball carrier is. Tackle types commonly made by a tackling player positioned in front of the ball carrier are known as profile tackles (FIG. 5), cut tackles (FIG. 4), angle tackles (FIG. 2), and roll tackles (FIG. 7). A profile tackle is made when the tackling player is almost face to face with the ball carrier at initial contact with the ball carrier, and at a height anywhere between the ball carrier's shoulders and mid-thighs (FIG. 5), and may occur when the ball carrier is often in the range of 337.5° to 0° to 22.5° from directly upfield of the tackling player, where 0° would place the ball carrier directly upfield of the tackling player 103. A cut tackle is made when the tackling player is almost face to face with the ball carrier at initial contact, when that contact is made at a lower height on the ball carrier's body than for a profile tackle (FIG. 4), and may occur when the ball carrier is often in the range of 337.5° to 0° to 22.5° range from the tackling player's horizontal field of vision 103. An angle tackle is made when the tackling player 202 is off to one side of the ball carrier 201 at initial contact, with the ball carrier still somewhat upfield from the tackling player just prior to contact with the ball carrier (FIG. 2). In an angle tackle, contact by the tackling player normally ends the ball carrier's ability to gain positive yardage, and the ball carrier is often in the ranges of either 22.5° to 90° or 270° to 337.5° from directly upfield of the tackling player 104. A ball carrier gains positive yardage while moving in a direction that is, at least in part, toward the end zone being defended by the tackling player. A roll tackle is made when the tackling player is to the side of the ball carrier at initial contact, and the tackling player's contact with the ball carrier most often does not end the ball carrier's ability to gain positive yardage (FIG. 7). With roll tackles, the ball carrier is often in the ranges of either 45° to 135° or 225° to 315° from directly upfield of the tackling player 105. Generally, when a tackle is made by a player positioned in front of the ball carrier, a more positive outcome may be achieved. Scoring for a player making a tackle from a position in front of the ball carrier may be increased if the more positive outcome results.

Figure 3:
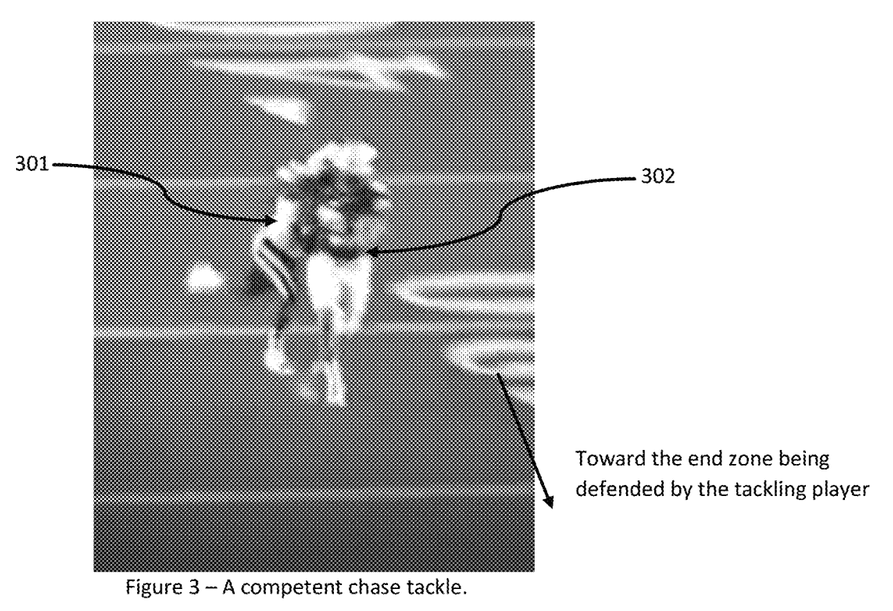
FIG. 3—A competent chase tackle.
Figure 6:
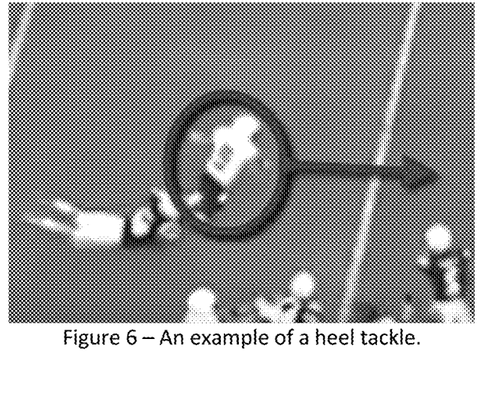
FIG. 6—An example of a heel tackle.

Other tackle types are made with the ball carrier positioned downfield from the tackling player, meaning that the ball carrier would be in front of the tackling player with the ball carrier facing the end zone being defended by the tackling player and the tackling player behind or beside the ball carrier while the ball carrier may be closer to end zone being defended by the tackling player's team than the tackling player is. Tackle types commonly made by a tackling player positioned behind or beside the ball carrier are known as roll tackles (FIG. 7), heel tackles (FIG. 6), and chase tackles (FIG. 3). A heel tackle is made when the tackling player is behind or to the side of the ball carrier at initial contact, then wraps his or her arms around the ball carrier's leg or legs, effectively tripping the ball carrier (FIG. 6). With heel tackles, the ball carrier is often within a range of 67.5° to 180° to 292.5° from directly upfield of the tackling player 106. A chase tackle is made when the tackling player 301 is behind the ball carrier 302 at initial contact, and the tackling player is able to wrap his or her arms around the ball carrier's hips and bring the ball carrier down (FIG. 3). With chase tackles, the ball carrier is often within a range of 135° to 225° from directly upfield of the tackling player 107. With both heel and chase tackles, the ball carrier is almost always able to gain positive yardage after initial contact. Generally, when a tackle is made by a player positioned to the side, or behind the ball carrier, a more negative outcome may be expected. Scoring for a player making a tackle from a position to the side or behind the ball carrier have a lower maximum score than positive outcome plays.

Figure 10:
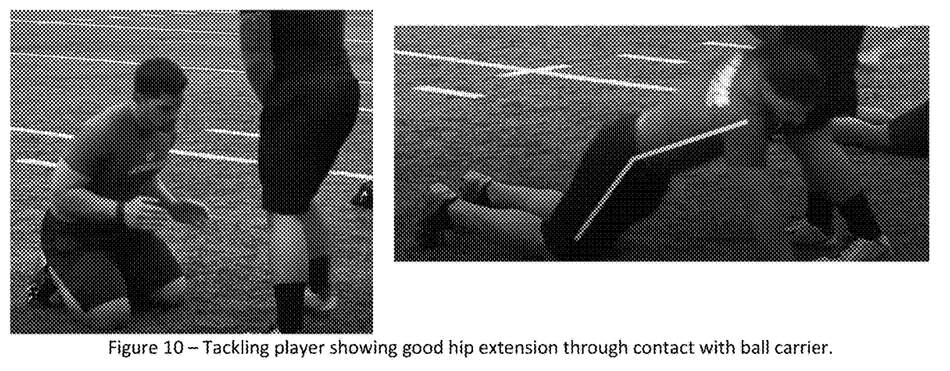
FIG. 10—Tackling player showing good hip extension through contact with ball carrier.
Figure 11:
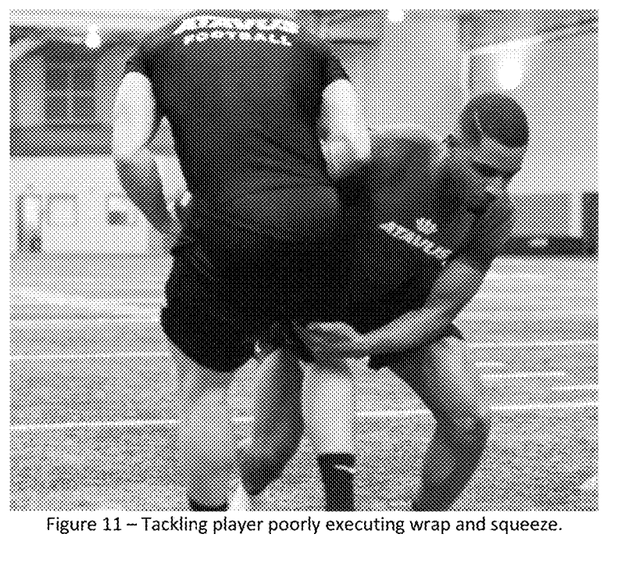
FIG. 11—Tackling player poorly executing wrap and squeeze.
Figure 12:
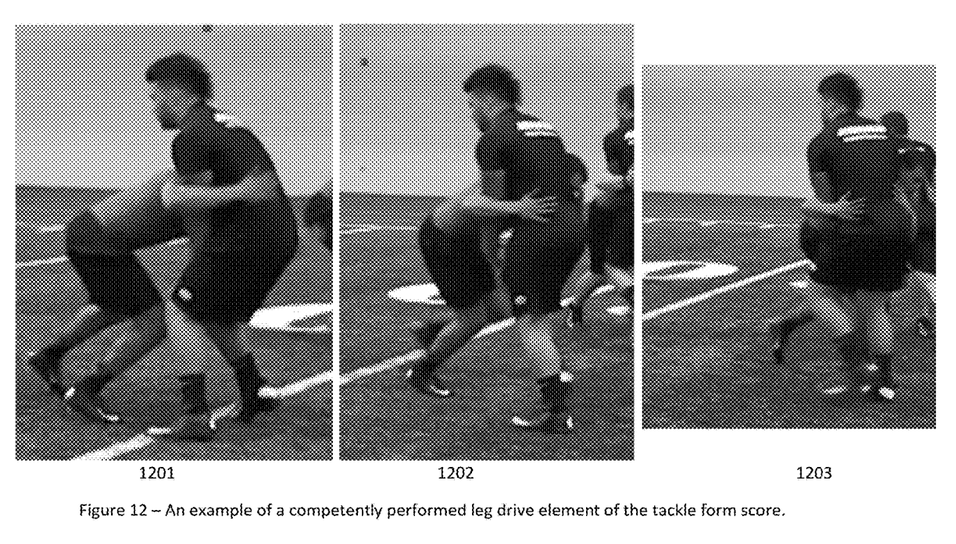
FIG. 12—An example of a competently performed leg drive element of the tackle form score.

In some embodiments, a tackle form score is used to evaluate player performance. A tackle form score may be based upon elements deemed essential to the act of completing an efficient tackle. The efficiency of a tackle, and therefore the tackle form score, may be evaluated in post-game video by examining elements of an efficient tackle, such as: the height at which contact is made 801; whether the tackling player's spine is in line 901; whether the tackling player uses the shoulder nearer to the ball carrier to make contact 802; whether the tackling player extends hands and arms past the ball carrier 803; whether the tackling player extends at the hip through the point of contact with the ball carrier (FIG. 10); whether the tackling player is able to wrap his or her arms around the ball carrier and squeeze the ball carrier (FIG. 11); and whether the tackling player continues to move his or her feet and legs after contact and hip extension (FIG. 12). Each of these elements may be assigned a weighting factor based on the element's importance to executing an efficient tackle. For example, the elements, in the order presented above, may be assigned weighting factors of: height—0.15, spine—0.15, near shoulder—0.25, arm extension—0.20, hip extension—0.10, wrap and squeeze—0.10, leg drive—0.05.

In at least one embodiment, the leg drive element is only scored in positive outcome situations.

In some embodiments, a score is given for each observable element of the tackle form. The scale of the scoring may be: zero for an element of an efficient tackle that was not observed, 0.5 for an element that was observed, but the element was executed poorly, and 1 for an element of an efficient tackle that was observed and executed competently. Examining each element under such a scoring scale, and to score each element with a 1, the scorer may examine post-game video for existence of: contact with the ball carrier made at a height to avoid helmet to helmet contact, usually targeting the area between the ball carrier's lower rib cage and the mid-thigh 801; the tackling player's spine in line during contact 901; the tackling player's use of his or her shoulder nearer to the ball carrier to make contact—in any situation other than being directly in front of or directly behind the ball carrier, one of the tackling player's shoulders will be physically nearer to the ball carrier and the tackling player should lead with the near shoulder into contact to receive a 1 score 802; the tackling player's hands and arms extending past the ball carrier after contact is made 803; the tackling player's hip joints extending as the near shoulder makes contact with the ball carrier (FIG. 10); the tackling player wraps his or her arms around the ball carrier, allowing the tackling player to squeeze, restrict the ball carrier's movement, and lead to an eventual tackle by the tackling player or another defensive player (FIG. 11 shows a poorly executed example since only one leg is weakly wrapped); the tackling player, after contact is made and arms are used to wrap the ball carrier, continues to push with alternating legs, using the additional force to push the ball carrier and eventually upend the ball carrier in a tackle (FIG. 12). Using the assigned weighting factors results in a perfect tackle form score of 1.00 for all elements being performed competently.

In some embodiments, a track form score is used to evaluate player performance. A track form score may be based upon elements deemed essential to the act of efficiently tracking a ball carrier to the point of contact. The tracking efficiency, and therefore the tracking form score, may be evaluated in post-game video by examining elements of efficient track form, such as: whether the tackling player closes space between him or herself and the ball carrier (FIG. 14); whether the tackling player uses effective movement to avoid obstacles (FIG. 13); whether the tackling player chooses an appropriate angle to move to the point of contact with the ball carrier (FIG. 15); whether the tackling player tracks the ball carrier's near hip to the contact point (FIG. 16); whether the tackling player maintains effective footwork to react effectively to ball carrier's rate of speed and change of direction (FIG. 17); whether the tackling player manages footwork to include powerful entry into the contact zone with the ball carrier. Each of these elements may be assigned a weighting factor based on the element's importance to executing an efficient tackle. For example, the elements, in the order presented above, may be assigned weighting factors of: closing space—0.20, avoiding obstacles—0.20, angle—0.15, near hip—0.15, footwork—0.10, contact zone—0.20.

In at least one embodiment, the contact zone element is only scored in positive outcome situations.

Figure 13:
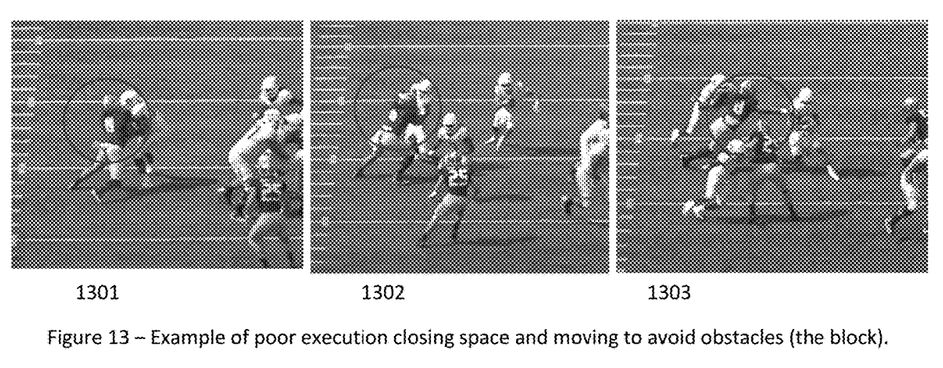
FIG. 13—Example of poor execution closing space and moving to avoid obstacles (the block).
Figure 14:
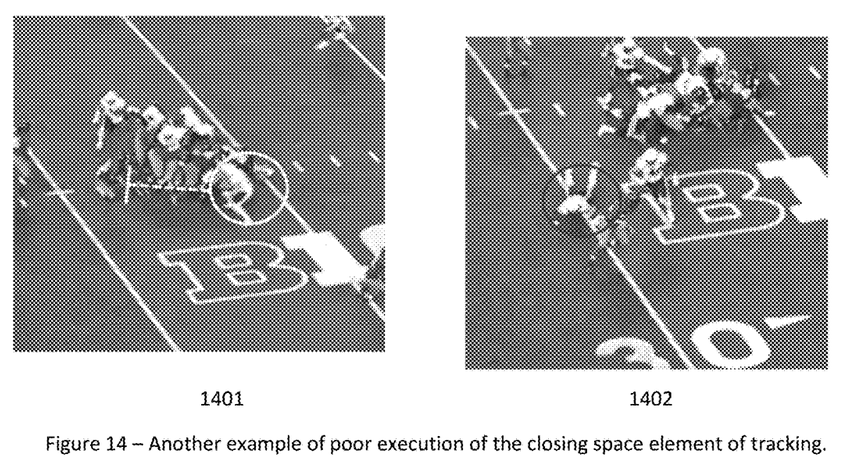
FIG. 14—Another example of poor execution of the closing space element of tracking.
Figure 15:
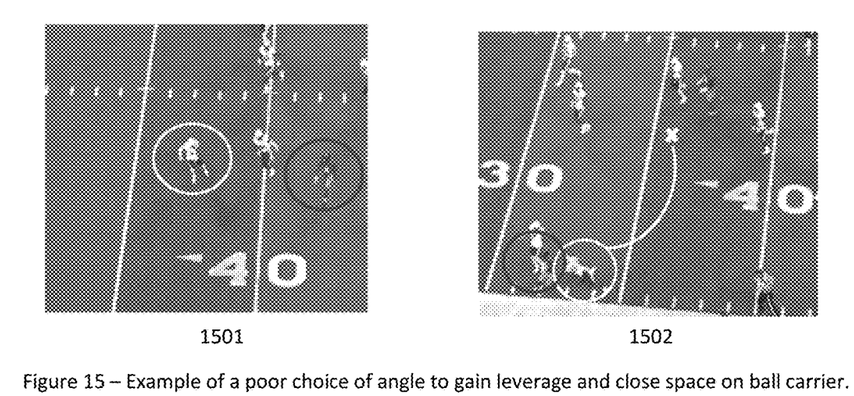
FIG. 15—Example of a poor choice of angle to gain leverage and close space on ball carrier.
Figure 16:
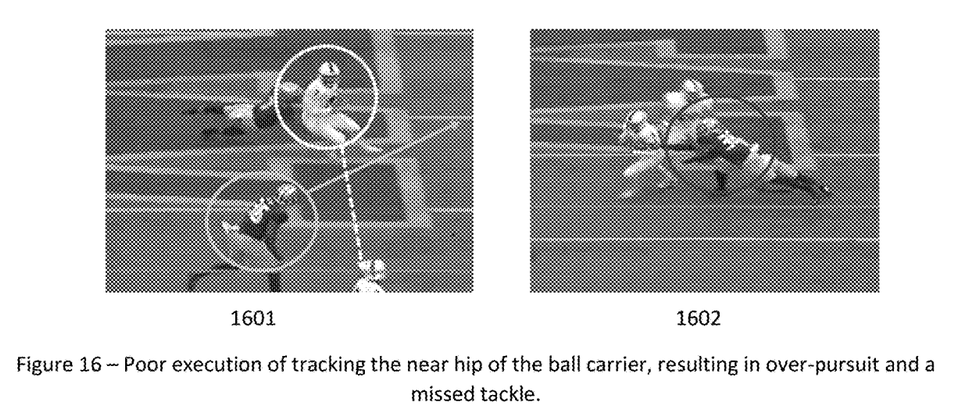
FIG. 16—Poor execution of tracking the near hip of the ball carrier, resulting in over-pursuit and a missed tackle.
Figure 17:
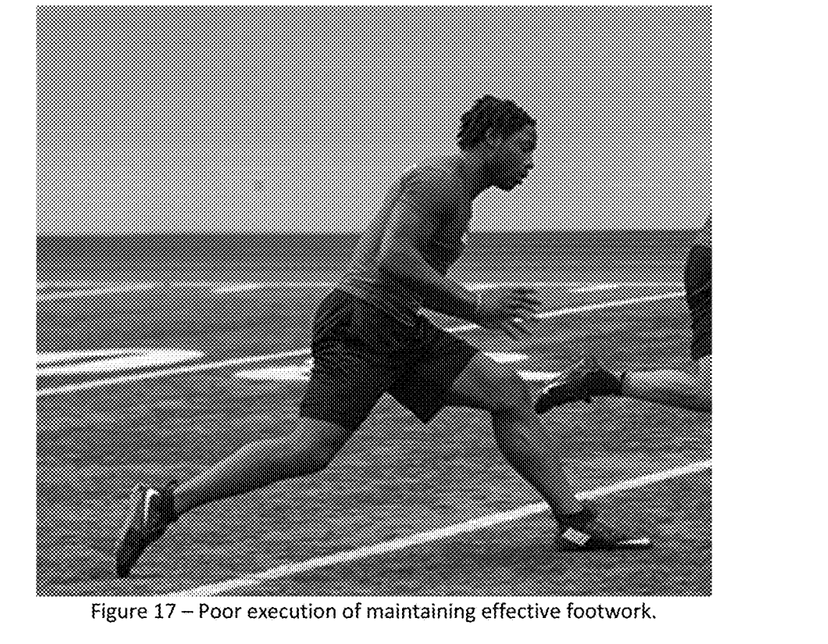
FIG. 17—Poor execution of maintaining effective footwork.

In some embodiments, a score is given for each observable element of the track form, whether the observation is that the element was performed correctly or that it was not performed correctly. The scale of the scoring may be: zero for an element of tracking efficiently that was not observed or executed so incorrectly it prevented the tackling player from making the tackle, 0.5 for an element that was observed, but the element was executed poorly, and 1 for an element of tracking efficiently that was observed and executed competently. Examining each element under such a scoring scale, and to score each element with a 1, the scorer may examine post-game video for existence of: the tackling player's effectiveness "closing space," or proactively reducing the distance, between him or herself and the ball carrier (an example of an incorrect execution and missed tackle is shown in FIG. 14); the tackling player's movements made to avoid obstacles between him or herself and the ball carrier, such as an opposing team player attempting to block the tackling player (an example of incorrect execution leading to a missed tackle is shown in FIG. 13); the tackling player's use of an efficient angle to engage the ball carrier while balancing other tracking elements like avoiding obstacles and closing space (an example of incorrect execution leading to a missed tackle is shown in FIG. 15); the tackling player tracks the ball carrier's near hip and does not overpursue the ball carrier (usually evidenced by ball carrier making a cut and evading the tackling player) (an example of incorrect execution leading to a missed tackle is shown in FIG. 16); the tackling player does not get caught flat-footed, in a wide, unsteady stance, or fall down prior to engaging in contact with the ball carrier (an example showing poor execution is shown in FIG. 17); the tackling player is able to initiate contact with the ball carrier in stride or with the ability to use lower body strength appropriate for good tackle form (i.e. ability to extend at the hip joint or joints, and the spine in line). Using the assigned weighting factors results in a perfect track form score of 1.00 for all elements being performed competently.

In some embodiments, a performance score is used to evaluate player performance. A performance score is based more on the results of the play, and how well the player could demonstrate track and tackle performance within the context of the game. A performance score is generated by a scorer who considers the following with respect to the player being scored: whether the tackling player was in a positive 101 or negative 102 situation as determined using the tackle circle (FIG. 1); the quality of the contact made by the tackling player on the ball carrier; the tackling player's ability to maintain an efficient angle and track to ball carrier; whether the ball carrier was able to gain positive yardage or if the tackle drove the ball carrier toward his own team's end zone (FIG. 18). The first step in determining the performance score is to place the tackle circle at initial contact between the tackling player and the ball carrier 703. The tackle circle should be centered on the tackling player, with the ball carrier more toward the edge of the tackle circle. The tackle circle, along with tackle type, if necessary, should then be used to determine whether the situation is positive or negative 703, see arrow in FIG. 7 indicating direction of tackling player, indicating a negative situation and likely roll tackle. Based on the situation, the player's performance is then examined and matched to the closest description of the performance observed for both tracking performance and tackling performance using the table of FIG. 18.

In one embodiment, a perfect performance score is 8 (FIG. 18). The performance score the player achieves may be divided by a perfect score to get a top perfect score of 1.00 to factor into an overall score without initially outweighing either the tackle form or track form score.

Figure 19:
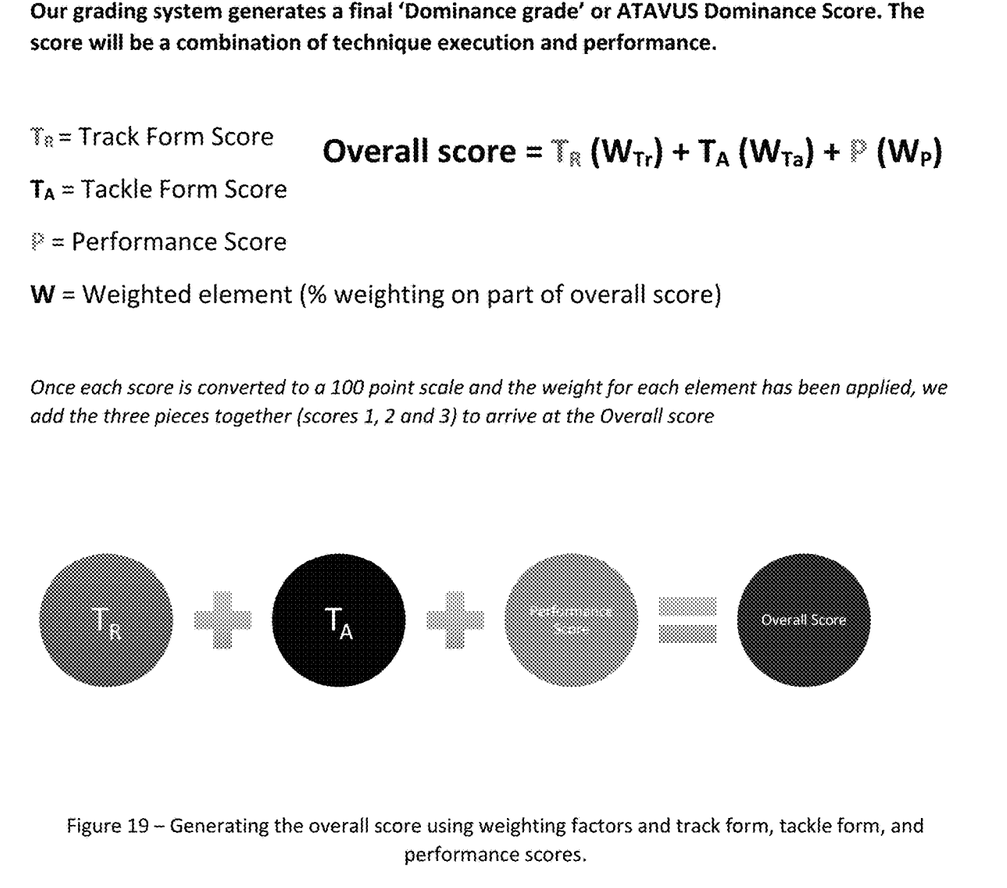
FIG. 19—Generating the overall score using weighting factors and track form, tackle form, and performance scores.

In some embodiments, an overall score is used. The overall score may comprise a composite and comprehensive scoring of all aspects of performance, and thus weighted amounts of tackle form, track form, and performance scores may be used in calculating an overall score (FIG. 19). Additionally, an overall score may be available for one individual play, though some scoring criteria may be absent from that play. An overall score may also be available for a range of a player's performance. For example, a player may receive an overall score for all scored plays over an entire game, over three games, or over 12 games. The overall score would then provide an indication of the player's average performance level, and over time indicate changes in the average performance level.

An example for how an overall score might be calculated would be to weight the trained skill scores each to 35% of an overall performance score, and then weight a performance score to 30% of an overall performance score. The result would be an overall performance score that balances all scoring criteria, with a small emphasis on trained skills over dealing positively with in-game situations that contribute to the performance score. In one embodiment, each component of the overall score may be weighted equally. In some embodiments, overall score weighting might be customized from game to game depending factors at the discretion of a coach, without regard allowing bias to affect the objectivity of the underlying scoring of player performance. For example, overall score weighting might be adjusted to recognize the perceived quality of the opposing team, the acute difficulty the opposing team's game plan presents, or the opposing team's overall speed.

Figure 20:
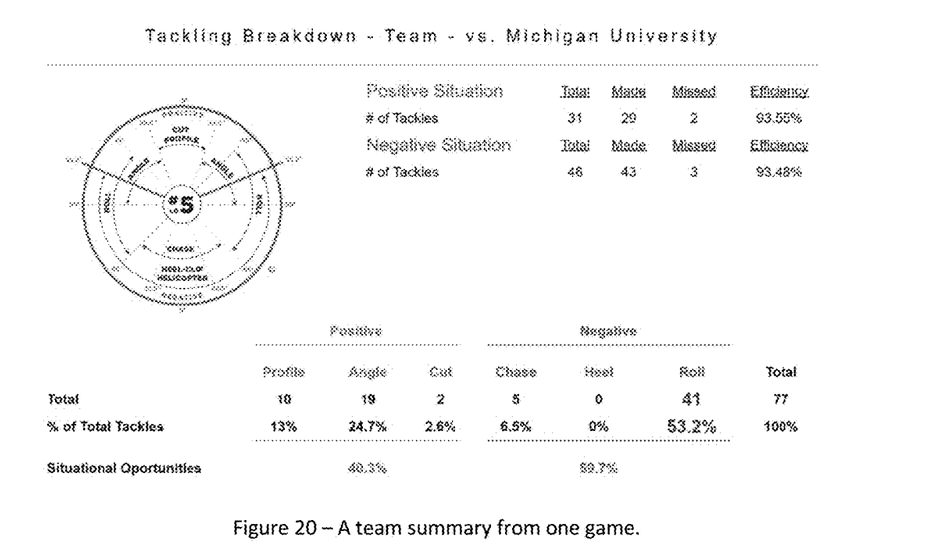
FIG. 20—A team summary—tackle efficiencies—from one game.

Further to generating scores for individual players over the course of an individual player's performance in a game or season, some embodiments of the present disclosure include generating information for a team's performance over a selected interval. For example, FIG. 20 shows a summary for one team's tackling efficiency performance, listing all tackle opportunities, how many of each of the different types of tackle were attempted, how many tackles were successfully executed, and whether the tackle was made in a positive outcome situation or a negative outcome situation.

Figure 21:
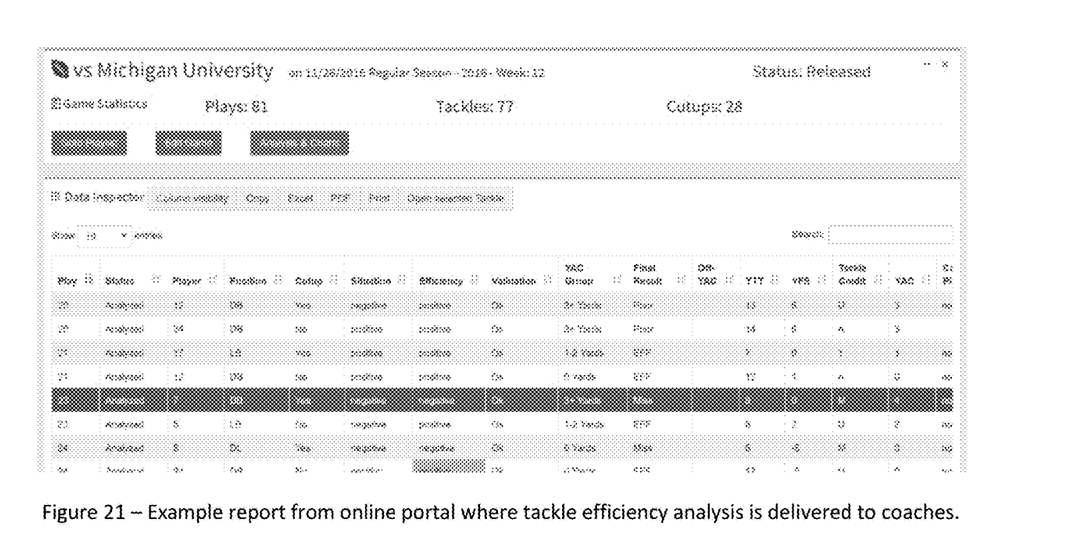
FIG. 21—Example report from online portal where tackle efficiency analysis is delivered to coaches.

Once all information has been gathered, it may be presented to coaches and players. In several embodiments, after evaluation, analysis, and scoring, are complete and data has been generated, the information is placed in an online portal that may be accessed by coaches, players, general management, coordinators, or any other party with a stake in the tackle efficiency of a team and its players. FIG. 21 shows an example report from one example of an online portal for delivery of information produced by the system and methods herein.

We claim:

1. A system of objectively evaluating a tackler's performance comprising:
   a video recording of a football game;
   a tackle circle configured to be applied to the video recording, wherein the center of the tackle circle is configured to be placed, in the video recording, at a tackler's point of contact with a ball carrier in the football game, wherein the applied tackle circle has a line parallel with on-field yard markings to bisect the tackle circle at 90 and 270 degree marks and the tackle circle's 180 degree mark is closer to an endzone being defended by the tackler; and
   a set of discrete skills the tackler is evaluated on during a tackle opportunity, wherein evaluating the tackler comprises:
      determining whether the ball carrier is within a zone of positive outcomes within the applied tackle circle opposite its 180 degree mark; and
      causing the set of discrete skills to be evaluated based, at least in part, on the determining.

2. The system of claim 1, wherein the set of discrete skills comprises:
   a set of tracking skills; and
   a set of tackling skills.

3. The system of claim 2, wherein the set of tracking skills comprises:
   the tackler closes space between the tackler and the ball carrier;
   the tackler uses effective movement to avoid obstacles;
   the tackler uses an appropriate angle to move to a point of contact with the ball carrier;
   the tackler tracks the ball carrier's nearest hip to the point of contact;
   the tackler maintains effective footwork to react to ball carrier's attempts to evade the tackler; and
   the tackler maintains a balanced posture when entering a zone of contact where the tackler will attempt to tackle the ball carrier.

4. The system of claim 2, wherein the set of tackling skills comprises:
   a height at which a tackle is made;
   the tackler's spine is in-line;
   the tackler uses his or her shoulder nearest to the ball carrier to make contact;
   the tackler extends hands and arms past the ball carrier at the point of contact;
   the tackler extends at the hip at the point of contact;

the tackler is able to wrap his or her arms around the ball carrier and squeeze; and the tackler continues to move legs and feet after contact and hip extension.

5. The system of any one of claims 1-4, wherein the tackle circle comprises a visual aid with markings to define a context of the tackle opportunity the tackler is evaluated upon.

6. The method of claim 5, wherein the tackler is additionally evaluated on at least one of the following:

scoring the tackler on a tackler's efficiency tracking the ball carrier, scoring the tackler on a tackler's efficiency tackling the ball carrier, or scoring the tackler based on an outcome of the tackle attempt.

7. A method of using a tackle circle as an evaluation tool for a tackle opportunity, the method comprising:

pausing playback of a video footage of a football play when a tackler who is defending an endzone reaches a point of contact with a ball carrier in the tackle opportunity;

in the paused playback of the video footage, applying the tackle circle by placing its center on the tackler at the point of contact, wherein the applied tackle circle has a line parallel with on-field yard markings to bisect the tackle circle at 90 and 270 degree marks and the tackle circle's 180 degree mark is closer to the endzone being defended by the tackler;

determining whether the ball carrier is within a zone of positive outcomes within the applied tackle circle opposite its 180 degree mark;

when the ball carrier is within the zone of positive outcomes, causing the tackle opportunity to be scored based on a first set of evaluation criteria corresponding to positive outcomes to obtain a tackle opportunity score;

when the ball carrier is not within the zone of positive outcomes, causing the tackle opportunity to be scored based on a second set of evaluation criteria not corresponding to positive outcomes to obtain a tackle opportunity score; and causing the obtained tackle opportunity score to be communicated to the tackler.

8. The method of claim 7, further comprising:

scoring the tackler a successful or unsuccessful attempt when the tackler has an opportunity to make a tackle.

9. The method of claim 8, wherein scoring the tackler on the tackler's efficiency tracking the ball carrier includes evaluating at least one of the following observable elements:

the tackler closes space between the tackler and the ball carrier, the tackler uses effective movement to avoid obstacles, the tackler uses an appropriate angle to move to the point of contact with the ball carrier, the tackler tracks the ball carrier's nearest hip to the point of contact, the tackler maintains effective footwork to react to ball carrier's attempts to evade the tackler, or the tackler maintains a balanced posture when entering a zone of contact where the tackler will attempt to tackle the ball carrier.

10. The method of claim 8, wherein scoring the tackler on the tackler's efficiency tackling the ball carrier includes evaluating at least one of the following observable elements:

a height at which the tackle is made, the tackler's spine is in-line, the tackler uses his or her shoulder nearest to the ball carrier to make contact, the tackler extends hands and arms past the ball carrier at the point of contact, the tackler extends at the hip at the point of contact, the tackler is able to wrap his or her arms around the ball carrier and squeeze, and the tackler continues to move legs and feet after contact and hip extension.

11. The method of claim 8, wherein scoring the tackler based on the outcome of the tackle attempt includes evaluating at least one of the following observable elements within a framework of expected positive outcome or expected negative outcome based on the tackle circle:

assigning a quality of the contact the tackler makes with the ball carrier, the tackler maintaining an efficient angle to track the ball carrier to the point of contact, or the tackler's effectiveness in preventing the ball carrier from gaining more yards after the point of contact.

\* \* \* \* \*